United States Patent
Pereira et al.

(10) Patent No.: US 11,179,491 B2
(45) Date of Patent: Nov. 23, 2021

(54) ADHESIVE COMPOSITION

(71) Applicant: TISSIUM SA, Paris (FR)

(72) Inventors: Maria Pereira, Lisbon (PT); Salim Adjili, Ivry sur Seine (FR)

(73) Assignee: Tissium SA, Paris (FR)

( * ) Notice: Subject to any disclaimer, the term of this patent is extended or adjusted under 35 U.S.C. 154(b) by 0 days.

(21) Appl. No.: 15/737,143

(22) PCT Filed: Jun. 17, 2016

(86) PCT No.: PCT/EP2016/064016
§ 371 (c)(1),
(2) Date: Dec. 15, 2017

(87) PCT Pub. No.: WO2016/202985
PCT Pub. Date: Dec. 22, 2016

(65) Prior Publication Data
US 2018/0177913 A1    Jun. 28, 2018

Related U.S. Application Data

(60) Provisional application No. 62/181,273, filed on Jun. 18, 2015.

(30) Foreign Application Priority Data

Jun. 18, 2015  (EP) .................................. 15172799

(51) Int. Cl.
| A61L 24/06 | (2006.01) |
| C08F 290/14 | (2006.01) |
| A61L 24/04 | (2006.01) |
| A61L 15/58 | (2006.01) |
| C08G 63/52 | (2006.01) |
| C09J 167/00 | (2006.01) |

(52) U.S. Cl.
CPC .............. *A61L 24/06* (2013.01); *A61L 15/58* (2013.01); *A61L 24/046* (2013.01); *C08F 290/141* (2013.01); *C08G 63/52* (2013.01); *C09J 167/00* (2013.01)

(58) Field of Classification Search
CPC ........ A61L 24/06; A61L 15/58; A61L 24/046; C08F 290/141; C08G 63/52; C09J 167/00
See application file for complete search history.

(56) References Cited

U.S. PATENT DOCUMENTS

| 5,866,632 A * | 2/1999 | Hashimoto |
| 2003/0078339 A1 | 4/2003 | Kiser et al. |
| 2009/0047256 A1 * | 2/2009 | Bettinger |
| 2014/0147472 A1 | 5/2014 | Elimelech et al. |
| 2014/0348896 A1 * | 11/2014 | Karp |

FOREIGN PATENT DOCUMENTS

| CN | 1993388 A | 7/2007 |
| CN | 101087860 A | 12/2007 |
| CN | 101111272 A | 1/2008 |
| CN | 101801322 A | 8/2010 |
| CN | 102176890 A | 9/2011 |
| CN | 102596275 A | 7/2012 |
| CN | 103083718 A | 5/2013 |
| CN | 103459529 A | 12/2013 |
| CN | 104144999 A | 11/2014 |
| EP | 1159015 A1 | 12/2001 |
| JP | A-S49-24245 | 3/1974 |
| JP | A-H2-238013 | 9/1990 |
| JP | T-2009-523864 | 6/2009 |
| JP | T-2016-526078 | 9/2016 |
| WO | WO 2000/051662 | 9/2000 |
| WO | WO 2012/042522 A2 | 5/2012 |
| WO | WO 2014/190302 A1 | 11/2014 |

OTHER PUBLICATIONS

Mohapatra (Journal of Chemical and Pharmaceutical Research, published 2014, pp. 1126-1134) (Year: 2014).*
Damink (Biomaterials, published 1996, pp. 765-773) (Year: 1996).*
International Search Report, issued by the European Patent Office, dated Aug. 26, 2016, 2 pp.

* cited by examiner

*Primary Examiner* — Alma Pipic

(57) ABSTRACT

A composition with improved adhesive and sealant properties comprising a) a pre-polymer comprising a polymeric unit of the general formula $(-A-B-)_n$, wherein A represents a substituted or un-substituted ester, B represents a substituted or un-substituted acid ester comprising at least two acid ester functionalities, and n represents an integer greater than 1, and b) an anhydride compound.

42 Claims, 6 Drawing Sheets

ADHESIVE COMPOSITION

CLAIM FOR PRIORITY

This is a National Stage Application under 35 U.S.C. § 371 of International Patent Application No. PCT/EP2016/064016, filed Jun. 17, 2016, which claims the benefit of EP 15172799.7, filed Jun. 18, 2015, which claims the benefit of U.S. Provisional Application No. 62/181,273, filed Jun. 18, 2015, all of which are incorporated herein by reference.

FIELD OF INVENTION

The present invention relates to a composition, a method of manufacturing the composition, a method of curing the composition, a cured composition obtainable therefrom, uses of the composition and methods of using the composition.

BACKGROUND OF THE INVENTION

Open heart surgery typically relies on a suture-based closure or attachment of cardiovascular structures. However, this can be technically challenging due to the fragility of young infant tissue and diseased or damaged adult tissue, leading to longer operative times, increased risk of complications of bleeding or dehiscence, and therefore worse outcomes. Furthermore, cardiopulmonary bypass (CPB) is required for open heart surgery, and this has significant adverse effects, including an inflammatory response and potential neurological complications.

While catheter-based interventions for closure of cardiac defects such as atrial and ventricular septal defects (ASDs and VSDs) have recently emerged in an effort to reduce the invasiveness of the procedures, major challenges remain with securing devices inside the beating heart. Specifically, fixation of devices for catheter-based closure of cardiac septal defects currently relies on mechanical means of gripping tissue. This can cause injury to critical structures, such as heart valves or specialized conduction tissue. Furthermore, if inadequate tissue rims exist around defects, the prosthesis may dislodge, damaging the neighboring structures and also leaving residual defects, limiting device application. Therefore, such methods can only be applied in select patients, depending on the anatomic location and the geometric shape of the defect.

Soft and compliant tissue adhesives that cure rapidly, have significant adhesive strength, are biocompatible and work in the presence of blood offer a potential solution. They could be used to attach tissue surfaces together or prosthetic devices to tissue without the need for mechanical entrapment or fixation, thereby avoiding tissue compression and erosion, and may also be utilized in minimally invasive surgical procedures. Such materials could find a broad range of applications not only in minimally invasive cardiac repair, but also in the repair of soft tissues potentially with minimal scarring and damage. For example, in vascular surgery, suture-based anastomosis does not always result in an instantaneous hemostatic seal, and can create irregularities in the endothelium that predispose to thrombosis. Furthermore, the presence of permanent sutures can cause a foreign body reaction with further inflammation and scarring at the repair site, which may increase the risk of late vessel occlusion. Tissue adhesives could accomplish such repairs with an instantaneous seal and with minimal scarring or tissue damage.

An ideal tissue adhesive, especially for cardiovascular and/or gastrointestinal applications, should have most of the following properties: (1) optimal viscosity or liquid-like properties prior to curing to enable easy application to a desired area while being retained at the application site, (2) minimum washout by body fluids and activation only when desired to facilitate its delivery and repositioning of implanted devices during minimally invasive procedures, (3) significant adhesive strength, especially in the presence of blood and/or other body fluids, (4) ability to resist the mechanical loads from adhesion to highly mobile tissue, for example contractions of the heart, or pulsations in large vessels, (5) ability to form a hemostatic seal, (6) minimal inflammatory response, and (7) biodegradability, which is especially important for pediatric applications since the long-term consequences of foreign materials in the growing body are uncertain.

Unfortunately, current clinically-available adhesives, such as medical grade cyanoacrylate (CA) or fibrin sealant, are easily washed out or cured under dynamic wet conditions, toxic and therefore cannot be used internally, and/or exhibit weak adhesive properties such that they cannot withstand the forces inside the cardiac chambers and major blood vessels. Also, many of these adhesives exhibit activation properties that make fine adjustments or repositioning of the devices very difficult. Moreover, many adhesives under development achieve tissue adhesion only through chemical reaction with functional groups at the tissue surface, and thus become ineffective in the presence of blood.

Alternatives to cyanoacrylate have been explored. U.S. Pat. No. 8,143,042 B2 describes biodegradable elastomers prepared by crosslinking a prepolymer containing crosslinkable functional groups, such as acrylate groups. It also discloses that it is desirable to increase the number of free hydroxyl groups on the polymer in order to increase the stickiness of the polymer. Increasing the number of hydroxyl groups in the backbone also leads to enhanced hydrophobicity solubility in physiologic solutions. This suggests that the primary mechanism of adhesion of the polymer is chemical interactions between functional groups, for example free hydroxyl groups on the polymer and the tissue to which it is applied. However, this type of chemical interaction becomes ineffective in the presence of body fluids, especially blood, as shown in Artzi et al., Adv. Mater. 21, 3399-3403 (2009).

Similarly, Mahdavi, et al., 2008, PNAS, 2307-2312, describes nanopatterned elastomeric polymer and proposes applying a thin layer of oxidized dextran with aldehyde functionalities (DXTA) to increase adhesion strength of the adhesive by promoting covalent cross-linking between terminal aldehyde group in DXTA with amine groups in proteins of tissue.

This adhesion mechanism based essentially on covalent bonding between the radicals generated during the curing process and functional groups of the tissue has several limitations. The use of adhesives with reactive chemistry requires tissue surfaces to be dried prior to application of the pre-polymer, which makes it very challenging to use in cardiac application, such as during emergency procedures. Additionally, reactive chemistry can denature proteins or tissue and promote undesirable immune reaction such as local inflammation which can lead to adhesive rejection. Moreover, reactive chemistry that only bonds to the surface of tissue would likely have lower adhesion as the interface would be more distinct, and thus there would be a mismatch in mechanical properties at the interface between the glue and tissue.

Elastomeric crosslinked polyesters are disclosed in US 20130231412 A1. Biodegradable polymers are disclosed in U.S. Pat. No. 7,722,894 B2. Adhesive articles are disclosed in WO2009067482 A1 and WO2014190302 A1. Blood resistant surgical glue is described in "A Blood-Resistant Surgical Glue for Minimally Invasive Repair of Vessels and Heart Defects" Sci Transl Med 8 Jan. 2014: Vol. 6, Issue 218, p. 218ra6, Nora Lang, Maria Pereira et al. and WO2014190302 A1. However, there still exists a need for an improved and commercially viable tissue sealant/adhesive that can be readily applied to the desired site, remains in place at the desired site prior to curing and is not washed away by bodily fluids, is biocompatible (non-toxic), and exhibits strong adhesive forces, such as those encountered inside the cardiac chambers and major blood vessels even in the presence of bodily fluids, such as blood.

SUMMARY OF THE INVENTION

The present invention provides a composition comprising:
a pre-polymer comprising a polymeric unit of the general formula $(-A-B-)_n$, wherein A represents a substituted or un-substituted ester, B represents a substituted or un-substituted acid ester comprising at least two acid ester functionalities; and n represents an integer greater than 1; wherein the composition comprises an anhydride compound.

The present invention also provides a method for manufacturing the composition according to the present invention.

The present invention further provides a method of curing the composition according to the present invention, comprising curing the composition with a stimulus, for example light in the presence of a photo-initiator.

The present invention also provides a cured composition obtainable by the curing method according to the present invention. According to preferred embodiment, said cured composition is an adhesive, i.e. is able of binding strongly to a surface or binding one surface to another.

The present invention further provides methods of use and use of the composition according to the present invention for gluing or sealing tissue or for adhering tissue to the surface of a medical device.

The present invention also provides a method for adhering tissue, the method comprising applying the composition according to the present invention to the surface of the tissue and curing the composition.

The present invention further provides a method for adhering tissue to the surface of a medical device, the method comprising applying the composition according to the present invention to the surface of the tissue and/or medical device and curing the composition. In preferred embodiments, a medical device can be adhered to another medical device, or parts of medical devices can be adhered together in the assembly of a medical device.

DETAILED DESCRIPTION OF THE INVENTION

Pre-Polymer

Figure 1:
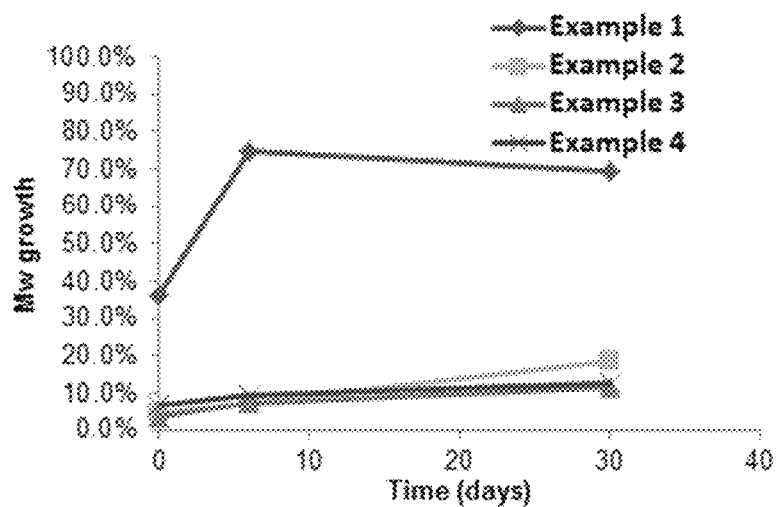
FIG. 1 is a graph displaying the change in Weight Average Molecular Weight (Mw) over time for compositions according to the present invention.

The pre-polymer according to the present invention comprises a polymeric unit of the general formula $(-A-B-)_n$, wherein A represents a substituted or un-substituted ester, B represents a substituted or un-substituted acid or acid ester comprising at least two acid or acid ester functionalities; and n represents an integer greater than 1.

Component A may be derived from a polyol, such as a diol, triol, tetraol or greater. Suitable polyols include diols, such as alkane diols; triols, such as glycerol, trimethylolpropane, triethanolamine; tetraols, such as erythritol, pentaerythritol; and higher polyols, such as sorbitol. Unsaturated diols, such as tetradeca-2,12-diene-1,14-diol, or other diols including macromonomer diols such as, for example polyethylene oxide, and N-methyldiethanoamine (MDEA) can also be used. Preferably, the polyol is substituted or unsubstituted glycerol.

Component B may be derived from a polyacid, such as a diacid or higher order acid. A wide variety of diacid, or higher order acids, can be used. Exemplary acids include, but are not limited to, glutaric acid (5 carbons), adipic acid (6 carbons), pimelic acid (7 carbons), sebacic acid (8 carbons), and azelaic acid (nine carbons). Exemplary long chain diacids include diacids having more than 10, more than 15, more than 20, and more than 25 carbon atoms. Non-aliphatic diacids can also be used. For example, versions of the above diacids having one or more double bonds can be used to produce polyol-diacid co-polymers. Preferably the diacid is substituted or unsubstituted sebacic acid.

Polyol-based polymers described in US Patent application Publication 2011-0008277, U.S. Pat. Nos. 7,722,894 and 8,143,042, the contents of which are hereby incorporated by reference, can also be used as a pre-polymer to form elastomeric polymeric materials.

Several substituents, such as amines, aldehydes, hydrazides, acrylates and aromatic groups, can be incorporated into the carbon chain. Exemplary aromatic diacids include terephthalic acid and carboxyphenoxy-propane. The diacids can also include substituents as well. For example, reactive groups like amine and hydroxyl can be used to increase the number of sites available for cross-linking. Amino acids and other biomolecules can be used to modify the biological properties. Aromatic groups, aliphatic groups, and halogen atoms can be used to modify the inter-chain interactions within the polymer.

The pre-polymer may further comprise a polyamide or polyurethane backbone. For example, polyamine (comprising two or more amino groups) may be used to react with polyacid together with polyol or after reacting with polyol. Exemplary poly(ester amide) includes those described in Cheng, et al., Adv. Mater. 2011, 23, 1195-11100, the contents of which are herein incorporated by reference. In other examples, polyisocianates (comprising two or more isocyanate groups) may be used to react with polyacid together with polyol or after reacting with polyol. Exemplary polyester urethanes include those described in US2013231412.

The weight average molecular weight of the pre-polymer, measured by Gel Permeation Chromatography equipped with a refractive index, may be from about 1,000 Daltons to about 1,000,000 Daltons, from about 1,000 Daltons to about 1,000,000 Daltons, preferably from about 2,000 Daltons to about 500,000 Daltons, more preferably from about 2,000 Daltons to about 250,000 Daltons, most preferably from about 2,000 Daltons to about 100,000 Daltons. The weight average molecular weight may be less than about 100,000 Dalton, less than about 75,000 Daltons, less than about 50,000 Daltons, less than about 40,000 Daltons, less than about 30,000 Daltons, or less than about 20,000 Daltons. The weight average molecular weight may be from about 1000 Daltons to about 10,000 Daltons, from about 2000 Daltons to about 10,000 Daltons, from about 3000 Daltons to about 10,000 Daltons from about 5,000 Daltons to about 10,000 Daltons. Preferably, it is about 3000 Daltons.

The term "about" as used herein means within 10%, preferably within 8%, and more preferably within 5% of a given value or range. According to a specific embodiment, "about X" means X, when X refers to the value or range.

The pre-polymer may have a polydispersity, measured by Gel Permeation Chromatography equipped with a refractive index, below 20.0, more preferably below 10.0, more preferably below 5.0, and even more preferably below 2.5. Preferably, it is about 2.5.

The pre-polymer may have a melt viscosity at 80° C. between 100 and 2000 cP, more preferably between 200 and 1000 cP and even more preferably between 300 and 500 cP.

The pre-polymer may have an acid number between 1 and 200 mg KOH/g of polymer, more preferably between 10 and 100 mg KOH/g of polymer, and even more preferably between 50 and 100 mg KOH/g of polymer. Preferably, it is about 80 mg KOH/g of polymer The molar ratios of the polyol to the polyacid in the pre-polymer may be 1:1, 1:2, 1:3, 1:4, 1:5, 1:6, 1:7, 1:8, 1:9 and 1:10, 10:1, 9:1, 8:1, 7:1, 6:1, 5:1, 4:1, 3:1, 2:1, 1:1. The molar ratios of polyol to the polyacid may also be 2:3, 3:2, 3:4, or 4:3. The polymer may also be the result of a mixture of two or more different ratios.

Activated Pre-Polymer

The pre-polymer of the present invention is preferably activated. It can be activated by introducing functional groups that can react or be reacted to form crosslinks. The pre-polymer is activated by reacting one or more functional groups on the pre-polymer backbone with one or more functional groups that can react or be reacted to form crosslinks resulting in cured polymer.

Suitable functional groups to be activated on the pre-polymer backbone include hydroxy groups, carboxylic acid groups, amines, and combinations thereof, preferably hydroxy and/or carboxylic acid. The free hydroxyl or carboxylic acid groups on the pre-polymer can be activated by functionalizing the hydroxy groups with a moiety which can form a crosslink between polymer chains. The groups that are activated can be free hydroxyl or carboxylic acid groups on A and/or B moieties in the pre-polymer.

The free hydroxy or carboxylic groups can be functionalized with a variety of functional groups, for example vinyl groups. Vinyl groups can be introduced by a variety of techniques known in the art, such as by vinylation or acrylation. According to the present invention, vinyl groups contain the following structure —$CR_1$=$CR_2R_3$ wherein $R_1$, $R_2$, $R_3$ are independently from one another, selected in the group consisting of H, alkyl such as methyl, ethyl, aryl such as phenyl, substituted alkyl, substituted aryl, carboxylic acid, ester, amide, amine, urethane, ether, and carbonyl.

Preferably, the functional group is or contains an acrylate group. According to the present invention, acrylate groups are moieties containing substituted or unsubstituted acryloyl group. The acrylate may contain the following group: —C(=O)—$CR_1$=$CR_2R_3$, wherein $R_1$, $R_2$, $R_3$ are independently from one another, selected in the group consisting of H, alkyl such as methyl or ethyl, aryl such as phenyl, substituted alkyl, substituted aryl, carboxylic acid, ester, amide, amine, urethane, ether, and carbonyl.

Preferably, $R_1$, $R_2$ and $R_3$ are H; or $R_1$ is $CH_3$, $R_2$ and $R_3$ are H; or $R_1$ and $R_2$ are H and $R_3$ is $CH_3$; or $R_1$ and $R_2$ are H and $R_3$ is phenyl.

Vinyl groups can also be incorporated in the backbone of the pre-polymer using free carboxyl groups on the pre-polymer. For example, hydroxyethyl methacrylate can be incorporated through the COOH groups of the pre-polymer using carbonyl diimidazole activation chemistry.

The degree of activation can vary and can be from 0.2 to 0.9 mol/mol of polyacid or polyol, preferably from 0.3 to 0.8 mol/mol of polyacid or polyol and most preferably from 0.4 to 0.6 mol/mol of polyacid or polyol, such as 0.5 mol/mol of polyacid or polyol for achieving optimal bust performance properties at room temperature or elevated temperature up to 40° C., preferably 37° C. It is most preferred when the degree of activation is as described above and the reactive functional group is acrylate i.e. degree of acrylation as above.

The activated pre-polymer preferably has the general formula (I):

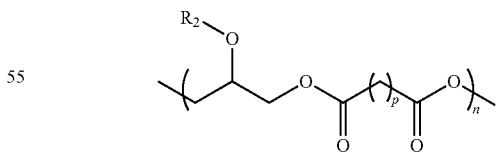

wherein n and p each independently represent an integer equal or greater than 1, and wherein $R_2$ in each individual unit represents hydrogen or a polymer chain or —C(=O)—$CR_3$=$CR_4R_5$, wherein $R_3$, $R_4$, $R_5$ are independently from one another, selected in the group consisting of H, alkyl such as methyl or ethyl, aryl such as phenyl, substituted alkyl, substituted aryl, carboxylic acid, ester, amide, amine, urethane, ether, and carbonyl.

Preferably, $R_3$, $R_4$ and $R_5$ are H; or $R_3$ is $CH_3$, $R_4$ and $R_5$ are H; or $R_3$ and $R_4$ are H and $R_5$ is $CH_3$; or $R_3$ and $R_4$ are H and $R_5$ is phenyl.

Preferably, p is an integer from 1-20, more preferably from 2-10, even more preferably from 4-10. It is most preferred when p=8.

The preferred pre-polymer has the following structure:

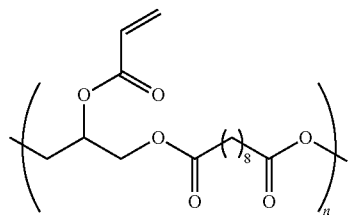

wherein n represents an integer equal or greater than 1

In addition to acrylates or other vinyl groups, other agents can be used to activate the pre-polymer. Examples of such agents include, but are not limited to, glycidyl, epichlorohydrin, triphenylphosphine, diethyl azodicarboxylate (DEAD), diazirine, divinyladipate, and divinylsebacate with the use of enzymes as catalysts, phosgene-type reagents, di-acid chlorides, bis-anhydrides, bis-halides, metal surfaces, and combinations thereof. Agents may further include isocyanate, aldehyde, epoxy, vinyl ether, thiol, DOPA residues or N-Hydroxysuccinimide functional groups.

The activated pre-polymer can be further reacted with one or more additional materials to modify the crosslinks between the polymer chains. For example, prior to or during curing/crosslinking, one or more hydrogel or other oligomeric or monomeric or polymeric precursors (e.g., precursors that may be modified to contain acrylate groups) such as poly(ethylene glycol), dextran, chitosan, hyaluronic acid, alginate, other acrylate based precursors including, for example, acrylic acid, butyl acrylate, 2-ethylhexyl acrylate, methyl acrylate, ethyl acrylate, acrylonitrile, n-butanol, methyl methacrylate, acrylic anhydride, methacrylic anhydride and TMPTA, trimethylol propane trimethacrylate, pentaerythritol trimethacrylate, pentaerythritol tetramethacrylate, ethylene glycol dimethacrylate. dipentaerythritol penta acrylate, Bis-GMA (Bis phenol A glycidal methacrylate) and TEGDMA (tri-ethylene, glycol dimethacrylate), sucrose acrylate; other thiol based precursors (monomeric or polymeric); other epoxy based precursors; and combinations thereof, can be reacted with the acrylated pre-polymer e.g. poly glycerol sebacate acrylate (PGSA).

The activated pre-polymer may be manufactured in the presence and/or mixed with a coloring agent. Preferred examples of coloring agents are the ones recommended by the FDA for use in medical devices, pharmaceutical products or cosmetics. See http://www.fda.gov/ForUndustry/ColorAdditives/ColorAdditiveInventories/.

Active Pre-Polymer Comprising Grafted Anhydrides

The anhydride compound of the composition according to the present invention may be generated from the activation of the pre-polymer, for example through the reaction of acryloyl chloride (AcCl) and free carboxylic acids. An example of such an anhydride has general formula (II):

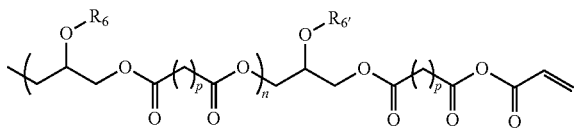

wherein p and n each individually represent an integer equal or greater than 1; wherein $R_6$ and $R_{6'}$ in each individual unit are independent and can be a polymer chain or $R_6$ and $R_{6'}$ in each individual unit are independent and can be —C(=O)—$CR_3$=$CR_4R_5$, wherein $R_3$, $R_4$, $R_5$ are independently from one another, selected from the group consisting of H, alkyl such as methyl or ethyl, aryl such as phenyl, substituted alkyl, substituted aryl, carboxylic acid, ester, amide, amine, urethane, ether, and carbonyl; or $R_6$ and $R_{6'}$ in each individual unit are independent and can be alkyl, aryl, heterocycles, cycloalkyl, aromatic heterocycles, multicycloalkyl, ester, ether, halide, carboxylic acid, amino, alkylamino, dialkylamino, trialkylamino, amido, carbamoyl, thioether, thiol, alkoxy, or ureido groups.

Preferably, p is an integer from 1-20, more preferably from 2-10, even more preferably from 4-10. It is most preferred when p=8.

The preferred anhydride has the following structure:

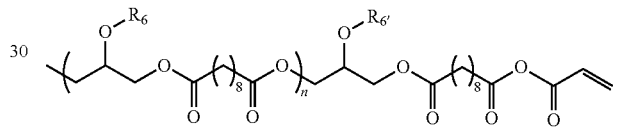

wherein $R_6$ or $R_{6'}$ independently represent a polymer chain or

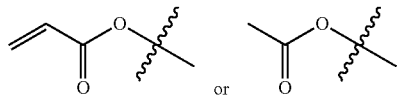

During activation of the pre-polymer, both asymmetric and symmetric anhydride can be generated. It is preferred that there is a higher content of asymmetric anhydride than its symmetric counterpart.

An assymetric anhydride (also referred as mixed anhydride) is a carboxylic acid anhydride that has the following general structural formula:

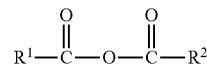

wherein R1 and R2 are different, and R1 and R2 are selected in the group of hydrogen atoms, alkyl groups, aryl groups.

A symmetric anhydride is a carboxylic acid anhydride that has the following general structural formula:

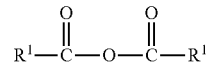

wherein R1 is selected in the group of hydrogen atoms, alkyl groups, aryl groups.

Preferably the molar ratio of the total grafted anhydride is above 0.02 mol/mol of polyacid, more preferably above 0.05 mol/mol of polyacid and even more preferably above 0.1 mol/mol of polyacid, as measured by nuclear magnetic resonance (NMR). This may also be the molar ratio of the total asymmetric grafted anhydride. Preferably the molar content of asymmetric anhydride is greater than 30% of the total dry anhydride content.

According to preferred embodiment, the asymmetric anhydride is stabilized to assure enhanced performance over time.

Hence, to improve the stability of the pre-polymer containing grafted anhydrides, unreacted nucleophilic groups may be partially or totally blocked or protected after pre-polymer activation. Examples of blocking or protection reactions are well known in the art. Hydroxyl protecting or blocking groups include acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; or cyclic or acylic, branched or unbranched, substituted or unsubstituted heteroalkynyl; substituted or unsubstituted aryl; or substituted or unsubstituted heteroaryl.

Preferably there are no free hydroxyl groups present on the pre-polymer. When there is low quantity free hydroxyls the content of total grafted anhydrides can be higher than 0.05 mol/mol of polyacid, as measured through NMR, and achieve enhanced stability as well as good adhesive and sealant properties.

Alternatively, in order to improve pre-polymer or composition stability, the methods of making and purifying the activated pre-polymer with grafted anhydrides should consider preferred conditions to avoid anhydride instability. For example, if the product is purified through water washings, conditions to allow a fast phase separation between organic and aqueous phase should be favored. For the present invention, phase separation during water washings can be improved by the use of salts solubilized in the aqueous phase. Examples of salts include but are not limited to, sodium chloride, sodium bicarbonate. In alternative, the salts produced during the reaction can be removed through filtration using an organic solvent such as ethyl acetate, n-methyl tetrahydrofurane, tetrahydrofurane.

Pre-Polymer Containing Non-Grafted Anhydrides

Additionally or alternatively, the anhydride compound of the composition according to the present invention may also be mixed with the pre-polymer, preferably the activated pre-polymer. The non-grafted anhydride according to the present invention is not especially limited, examples including acrylic anhydride, methacrylic anhydride, 4-methacryloyloxyethyl trimellitate anhydride, succinic anhydride, maleic anhydride or any combination thereof. Preferably the anhydride comprises acrylic anhydride or methacrylic anhydride.

Preferably the amount of anhydride present in the composition is in the range of 1 to 10 wt %, by total weight of the composition. The presence of anhydride increases adhesive properties of the cured composition with a preferred range of 1 to 10 wt %, as measured by weighing, for providing optimal adhesive properties. Preferred content is between 3 and 6 wt %.

Curing

The composition according to the present invention can be a surgical composition and can be used as tissue sealants and/or adhesives. The composition has flow characteristics such that they can be applied to the desired area through a syringe or catheter but is sufficiently viscous to remain in place at the site of application without being washed away by bodily fluids, such as water and/or blood. Preferably, the viscosity of the composition is 500 cP to 100000 cP, more preferably 1000 to 50000 cP, even more preferably 2000 to 40000 cP and most preferably 2500 to 25000 cP. Viscosity analysis is performed using a Brookfield DV-II+Pro viscosimeter with a 2.2 mL chamber and SC4-14 spindle, the speed during the analysis is varied from 5 to 80 rpm. The above mentioned viscosity is present in the relevant temperature range for medical application i.e. room temperature up to 40° C., preferably 37° C.

The composition is also sufficiently hydrophobic to resist washout by bodily fluids, such as blood. This facilitates delivery to the desired site as well as repositioning of devices implanted using the composition of the invention during minimally invasive surgery. Hydrophobicity is dependent on the chemical composition of the pre-polymer, including the hydrophobic nature of the polymer backbone (for example longer alkyl chain are more hydrophobic than shorter chains) and the degree of activation. Preferably there are no free hydroxyl groups on the pre-polymer of the uncured composition nor are there free hydroxyl groups present in the cured composition. The pre-polymer of the present invention may already contain crosslinks before curing, but typically is not fully crosslinked as it is soluble in organic solvents such as dichloromethane or ethyl acetate. The composition of the invention may be incubated in bodily fluids, such as blood, prior to administration and curing, without a substantial decrease in adhesive strength when cured.

The composition of the invention is stable in bodily fluids, such as blood. More particularly, the composition of the invention does not spontaneously crosslink in bodily fluids absent the presence of an intentionally applied stimulus such as light, for example UV light, heat, or chemical initiator to initiate crosslinking.

The composition can be cured using a free radical initiated reaction, such as, for example, by photo-initiated polymerization, thermally-initiated polymerization, and redox initiated polymerization.

Preferably, the composition is irradiated with light, for example ultraviolet (UV) light in the presence of a photoinitiator to facilitate the reaction. Examples of suitable photoinitiators include, but are not limited to: 2-dimethoxy-2-phenyl-acetophenone, 2-hydroxy-1-[4-(hydroxyethoxy)phenyl]-2-methyl-1-propanone (Irgacure 2959), 1-hydroxycyclohexyl-1-phenyl ketone (Irgacure 184), 2-hydroxy-2-methyl-1-phenyl-1-propanone (Darocur 1173), 2-benzyl-2-(dimehylamino)-1-[4-morpholinyl) phenyl]-1-butanone (Irgacure 369), methylbenzoylformate (Darocur MBF), oxy-phenyl-acetic acid-2-[2-oxo-2-phenyl-acetoxyethoxy]-ethyl ester (Irgacure 754), 2-methyl-1-[4-(methylthio)phenyl]-2-(4-morpholinyl)-1-propanone (Irgacure 907), diphenyl(2,4,6-trimethylbenzoyl)-phosphine oxide (Darocur TPO), phosphine oxide, phenyl bis(2,4,6-trimethyl benzoyl) (Irgacure 819), and combinations thereof.

Preferably, the composition is irradiated with visible light (typically blue light or green light) in the presence of a photoinitiator to facilitate the reaction. Examples of photoinitiators for visible light include, but are not limited to, diphenyl(2,4,6-trimethylbenzoyl)-phosphine oxide, eosin Y disodium salt, N-Vinyl-2-Pyrrolidone (NVP) and triethanolamine, and camphorquinone.

In applications of the composition involving in vivo photopolymerization and other medical applications, the use of cytocompatible photoinitiators is preferred and may be required by regulatory agencies. Photoinitiator Irgacure 2959 may be used which causes minimal cytotoxicity (cell death) over a broad range of mammalian cell types and species.

In order for the photopolymerization to occur, the composition (and the substrate to which is it applied, if applicable) is preferably sufficiently transparent to the light.

In applications when the composition is cured in vivo, the temperature at which curing occurs is preferably controlled as not damage the tissue on which the composition has been applied. Preferably, the composition is not heated above 45° C. during irradiation, more preferably not above 37° C., and even more preferably not above 25° C.

In addition to photochemical crosslinking, the composition can be cured thermally, by Mitsunobu-type reaction, by redox-pair initiated polymerization for example benzoyl peroxide, N,N,-dimethyl-p-toluidine, ammonium persulfate, or tetramethylenediamine (TEMED), and by a Michael-type addition reaction using a bifunctional sulfhydryl compound.

Upon polymerization, the pre-polymer forms a cross-linked network with improved adhesive properties and exhibits significant adhesive strength even in the presence of blood and other bodily fluids. The adhesive of the Invention obtained after curing is preferably sufficiently elastic to resist movement of the underlying tissue, for example contractions of the heart and blood vessels. The adhesive can provide a seal, preventing the leakage of fluids or gas. The adhesive is preferably biodegradable and biocompatible, causing minimal inflammatory response. The adhesive is preferably elastomeric.

Biodegradability can be evaluated in vitro, such as in phosphate buffered saline (PBS) or in acidic or alkaline conditions. Biodegradability can also be evaluated in vivo, such as in an animal, for example mice, rats, dogs, pigs or humans. The rate of degradation can be evaluated by measuring the loss of mass of the polymer over time in vitro or in vivo.

The cured composition, alone or coated on a patch or tissue exhibits a 90° pull off adhesive strength of at least 0.5 N/cm$^2$, preferably at least 1 N/cm$^2$ and even more preferably at least 2 N/cm$^2$, for example 1.5N/cm$^2$ to 2N/cm$^2$, but preferably greater than 5 N/cm$^2$, for example up to 6 N/cm$^2$ or 7 N/cm$^2$ or greater. Pull off adhesive strength refers to the adhesion value obtained by attaching an adhesive article or sample to wet tissue, such as epicardial surface of cardiac tissue, blood vessels, or the aerosol side of porcine intestine tissue, immobilized on a flat substrate, such as a metallic stub. The 90° pull off adhesion test determines the greatest perpendicular force (in tension) that a surface area can bear before adhesive detachment.

According to preferred embodiment, the composition of the invention is cured in light and in presence of a photo initiator and the cured composition exhibits a 90° pull off adhesive strength of at least 0.5 N/cm$^2$, preferably at least 1 N/cm$^2$ and even more preferably at least 2 N/cm$^2$, for example 1.5N/cm$^2$ to 2N/cm$^2$, but preferably greater than 5 N/cm$^2$, for example up to 6 N/cm$^2$ or 7 N/cm$^2$ or greater.

The cured composition can also exhibit a burst pressure of greater than 100 mmHg, preferably in the range of 400 mmHg to 600 mmHg or greater, for example 400 mmHg or 500 mmHg. Burst pressure or strength refers to the pressure value obtained to burst an explanted porcine carotid arterial vessel which has an incision coated with the composition.

The composition of the present invention when cured in light and in the presence of a photo-initiator preferably has one or more of the following properties:

i) 90° pull off strength greater than 1.5 N/cm$^2$, preferably 2 to 7 N/cm$^2$ or greater; and ii) burst performance of greater than 100 mmHg, preferably 400 to 500 mmHg or greater.

According to preferred embodiment, the composition of the invention is used as adhesive, i.e. is able after curing of binding strongly to a surface or binding one surface to another.

According to alternative embodiment, the composition of the invention is used as sealant, i.e. is able after curing of preventing leaking (e.g. fluid, gas) by forming a barrier or filling a void volume.

Besides adhesion and sealing of wet biological tissue, the composition can adhere to and seal a variety of hydrophilic or hydrophobic substrates, natural or synthetic, including polyethylene terephthalate, expanded polyethylene terephthalate, polyester, polypropylene, silicones, polyurethanes, acrylics, fixed tissue (e.g. pericardium), ceramics or any combinations thereof.

Method of Manufacture

The method for manufacturing the composition of the present invention comprises:

i) polycondensation of a first component comprising two or more functionalities of the general formula —OR, where R of each group is independently hydrogen or alkyl; and a second component comprising two or more acid ester functionalities;

ii) activation of the pre-polymer made by step i);

iii) formation or addition of an anhydride compound; optionally iv) blocking free hydroxyl groups; and/or optionally v) purification of the activated pre-polymer made by steps ii) and/or iii) and/or iv).

The said first component may be a polyol, such as a diol, triol, tetraol or greater. Suitable polyols include diols, such as alkane diols; triols, such as glycerol, trimethylolpropane, triethanolamine; tetraols, such as erythritol, pentaerythritol; and higher polyols, such as sorbitol. Unsaturated diols, such as tetradeca-2,12-diene-1,14-diol, or other diols including macromonomer diols such as polyethylene oxide, and N-methyldiethanoamine (MDEA) can also be used. Preferably, the polyol is substituted or unsubstituted glycerol.

The said second component may be a polyacid, such as a diacid or higher order acid. A wide variety of diacid, or higher order acids, can be used. Exemplary acids include, but are not limited to, glutaric acid (5 carbons), adipic acid (6 carbons), pimelic acid (7 carbons), sebacic acid (8 carbons), and azelaic acid (nine carbons). Exemplary long chain diacids include diacids having more than 10, more than 15, more than 20, and more than 25 carbon atoms. Non-aliphatic diacids can also be used. For example, versions of the above diacids having one or more double bonds can be used to produce polyol-diacid co-polymers.

Exemplary aromatic diacids include terephthalic acid and carboxyphenoxy-propane. The diacids can also include substituents as well, for example amine and hydroxyl substituents.

Preferably the diacid is substituted or unsubstituted sebacic acid.

The said first and second component are added together in a first component:second component molar ratio range of 0.5:1 to 1.5:1, preferably 0.9:1.1 and most preferred 1:1.

Where the first component is glycerol and the second component is sebacic acid and added in a 1:1 molar ratio, there are three hydroxyl groups on glycerol for two carboxyl groups on the sebacic acid. Therefore the extra hydroxyl group on glycerol is used during the activation step.

The conditions for step i) are not especially limited but may include a temperature range of 100 to 140° C., preferably 120 to 130° C., an inert atmosphere, preferably comprising nitrogen, and under vacuum.

The activating agent of step ii) is preferably an acrylating agent which comprises an acrylate group which are moieties containing substituted or unsubstituted acryloyl group. The acrylate may contain the following group: —C(=O)—$CR_1$=$CR_2R_3$, wherein $R_1$, $R_2$, $R_3$ are independently from one another, selected in the group consisting of H, alkyl such as methyl or ethyl), aryl such as phenyl, substituted alkyl, substituted aryl, carboxylic acid, ester, amide, amine, urethane, ether, and carbonyl.

Preferably, $R_1$, $R_2$ and $R_3$ are H; or $R_1$ is $CH_3$, $R_2$ and $R_3$ are H; or $R_1$ and $R_2$ are H and $R_3$ is $CH_3$; or $R_1$ and $R_2$ are H and $R_3$ is phenyl.

Most preferably, the acrylating agent is acryloyl chloride.

Steps i) to iv) can be carried out in the presence of one or more solvents or catalysts, examples including dichloromethane (DCM), ethyl acetate (EtOAc) dimethylaminopyridine (DMAP), and triethylamine (TEA) or any combination thereof.

The purification step v) is carried out to ensure that any solvents and un-reacted products are removed from the pre-polymer made by step iii) and iv). This purification step can comprise filtration and/or water washing. For the present invention, it has been shown that phase separation during water washings can be improved by the use of salts solubilized in the aqueous phase (e.g. from about 50 to about 500 g/L salt aqueous solution, preferably about 300 g/L salt, for example sodium chloride, aqueous solution). It is thus most preferred when the water washing is salted water washing. Examples of salts include but are not limited to, sodium chloride, sodium bicarbonate. According to a preferred alternative embodiment, the salts produced during said reaction can be removed through salt precipitation using an organic solvent such as ethyl acetate, n-methyl tetrahydrofurane, tetrahydrofurane followed by purification. Purification through filtration after salt precipitation for example in presence of ethyl acetate might not able to reduce enough the salt content in composition of the invention therefore, an additional salted water wash (e.g. with 200 g/L sodium chloride in water) can be performed.

The inventors have shown that an increased amount of anhydrides and purification with salted water wash, particularly NaCl, demonstrates a synergistic effect of unexpectedly high adhesion, good sealant properties such as burst performance, as well as enhanced stability. This is also demonstrated when filtration is used followed by salted water wash.

The purification step may also preferably be followed by one or more, more preferably all of the following steps including addition of free radical inhibitor, for example butylated hydroxytoluene (BHT), monomethylether-hydroquinone (MEHQ), phenylbutyl-nitrone (PBN), and/or photoinitiator, for example Irgacure 2959 or diphenyl-trimethyl-phosphine oxide (TPO), solvent evaporation and/or extraction, preferably through supercritical $CO_2$ to assure efficient solvent and impurities removal without interfering with the activation of the pre-polymer.

Special Embodiment A: Manufacture of Composition with Grafted Anhydrides (Formation of Anhydrides During Activation Step with Acrylating Agent)

During the acrylation process, anhydrides can be formed resulting from the reaction of the acrylated monomer with any carboxylic acid groups (step iii)). To enhance the stability of the anhydride groups, hydroxyl blockage or protection may be performed (step iv)). Techniques known in the art can be applied. Preferably, the hydroxyls are blocked through acylation using a compound such as ethanoyl chloride.

As indicated above, to improve stability of the pre-polymer containing grafted anhydrides, unreacted nucleophilic groups may be partially or totally blocked or protected after pre-polymer activation. Examples of blocking or protection reactions are well known in the art. Hydroxyl protecting or blocking groups include acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; or cyclic or acylic, branched or unbranched, substituted or unsubstituted heteroalkynyl; substituted or unsubstituted aryl; or substituted or unsubstituted heteroaryl.

Similarly, in order to improve pre-polymer or composition stability, the methods of making and purifying the activated pre-polymer with grafted anhydrides should consider preferred conditions to avoid anhydride instability. For example, if the product is purified through water washings, as mentioned above.

Special Embodiment B: Manufacture of Composition with Non-Grafted Anhydrides (Addition of Anhydrides)

Additionally or alternatively, anhydrides are added after activation of the pre-polymer, preferably after purification step v) and followed by mixing. The anhydride used according to the present invention is not especially limited, examples including methacrylic anhydride, acrylic anhydride, 4-methacryloyloxyethyl trimellitate anhydride, succinic anhydride, maleic anhydride and any combination thereof. Preferably the anhydride comprises methacrylic anhydride or acrylic anhydride.

Preferably the amount of anhydride added in the composition is in the range of 1 to 10 wt %, by total weight of the composition. The presence of anhydride increases adhesive properties with a preferred range of 3 to 6 wt % for providing optimal adhesive properties.

The anhydride may be mixed in situ with the pre-polymer and immediately applied to the targeted substrate, for example using a double barrel syringe. The anhydride may also be mixed in the pre-polymer and then stored; in this scenario, and to increase the stability of the formulation in the presence of anhydride functional groups, hydroxyl groups may be blocked in the activated pre-polymer.

Residual levels of grafted anhydrides may also be present, preferably at a level below 0.05 mol/mol of polyacid. The content of anhydride content can be controlled by ethanol capping or using any other nucleophilic substitution reaction. Suitable reagents include alcohols, amines or sulfhydryl compounds. The addition of ethanol is preferably at a temperature in the range of 30 to 50° C., for example 40° C. The duration of the ethanol capping step is conducted preferably during 10 and 40 hours, more preferably during 24 hours. The volumetric ratio of polymer solution to ethanol is in the range of 20:1, more preferably in the range of 10:1 and even more preferably in the rage of 5:1.

The formation of grafted anhydrides may also be prevented through blockage of any free carboxylic acid groups prior to activation.

Methods of Using

The composition can be applied directly to the desired site, such as by application with syringe or a catheter, through a spreading tip, by spraying or using a brush. The composition preferably is sufficiently non-viscous as to be injectable through a syringe needle having a gauge of 14 to 20, preferably 14 to 18 but sufficiently viscous to remain in place at the site of administration with minimum washout. The composition can be mixed before application or during application with a photoinitiator, stabilizer, therapeutic, prophylactic, and/or diagnostic agent, and/or one or more excipients.

The materials can be used directly, i.e., applied directly to the site to be adhered or sealed. Alternatively, the materials can be applied to a device, such as a patch or tape, to adhere the patch to the desired site. Conventional patch, patch materials or graft materials, natural or synthetic, known in the art can be used. Patches for use with major blood vessels, cardiac tissue, and/or hard to treat wounds (e.g., diabetic ulcers) are known in the art. Biocompatible, biodegradable surgical tape can be used, for example, to stop bleeding during surgery. Since the tape is biodegradable, it does not need to be removed before the surgeon sutures the wound closed. Examples of other suitable materials include polyethylene terephthalate, expanded polyethylene terephthalate, polyester, polypropylene, silicones, polyurethanes, acrylics, fixed tissue (e.g. pericardium), ceramics or any combinations thereof.

The thickness of the composition or adhesive layer can be varied depending on the application and site of administration. The thickness of the coatings can be at least about 50 microns, 60 microns, 70, microns, 74 microns, 75 microns, 80 microns, 100 microns, 125 microns, 150 microns, 175 microns, 200 microns, 225 microns, 250 microns, 275 microns, 300 microns, 325 microns, 350 microns, 375 microns, 400 microns, 425 microns, 450 microns, 475 microns, 500 microns, 525 microns, 550 microns, 575 microns, 600 microns, 625 microns, 650 microns, 675 microns, 700 microns, or 725 microns.

The adhesive and sealing properties of the activated pre-polymer can be induced through different approaches. The preferred approach is through a light stimulus in the presence of a photoinitiator. Other potential stimuli include heat in the presence of suitable initiators known in the art, or the use of reactive chemicals that can induce the network polymerization as disclosed above.

The adhesive strength may be improved by subjecting the composition to preload during curing. This may be particularly useful for those embodiments involving a patch where the prepolymer is coated on a patch and then applied to a tissue. The preload applied in the coated patch during curing can vary provided it results in an improvement in adhesive strength. The preload force applied to the patch may be from about 0.5 N to about 10 N, preferably from about 1 N to about 8 N, more preferably from about 2 N to about 8 N, most preferably from about 3 N to about 7 N. The application of preload may help the adhesive penetrate into the tissue.

Uses

A. Tissue Adhesion and Sealing

The composition according to the invention may be used for adhering or sealing targeted surfaces including tissue, graft material such as PTFE-based graft, or any combination thereof.

The method for adhering or sealing targeted surfaces comprises applying the composition to the surface and curing the composition.

Unlike conventional tissue adhesives that spontaneously activate during application or in the presence of water, or adhesives that are hydrophilic and thus are subject to washout prior to curing, the composition according to the invention can be applied to wet substrates without activation or displacement. The composition can also be applied to dry substrates.

The composition may also be used for adhering tissue to the surface of a medical device. The composition can be used in medical devices, either as part or all of a device or to adhere a device to tissue. The method for adhering tissue to the surface of a medical device comprises applying the composition to the surface of the tissue and/or medical device and curing the composition. The composition can also be used to join tissue, including one or more tissue in vivo.

Surgical adhesives comprising the composition according to the invention can also be used. Examples of applications include to stop bleeding, for example, due to a wound or trauma or during surgery such as after suturing a graft to a vessel or after vascular access in endovascular procedures. The adhesive does not need to be removed before the surgeon sutures the wound closed since it will degrade over time. Other types of wounds that can be treated include, but are not limited to, wounds that leak, wounds that are hard to close or that fail to heal properly through normal physiologic mechanisms. The application can be performed both inside or outside the body, for human or veterinary use.

The composition according to the invention can also be fabricated into a biodegradable stent. The stent can increase the diameter of a blood vessel to increase flow through the vessel, but since the stent is biodegradable, the blood vessel can increase in diameter with a reduced risk of thrombosis or covering the stent with scar tissue, which can re-narrow the blood vessel. The composition can cover an outer surface of a stent to help adhere the stent to a vessel wall in a manner that is less damaging to the tissue than an uncovered stent or avoid its displacement inside the body. Similarly, the composition can cover the surface of any devices which are in contact with tissue to provide a suitable interface that can be adhesive to tissue.

The composition according to the present invention can be used in a variety of other applications where an adhesive or sealant is required. These include, but are not limited to, air leaks following a lung resection; to reduce the time for surgical procedures; to seal dura; to ease laparoscopic procedures; as a degradable skin adhesive; as a hernia matrix to prevent or to reduce the need for stables or tacks; to prevent blood loss; to manipulate organs or tissues during surgical procedures; to secure corneal transplants in place; to patch a heart to deliver drugs and/or to reduce dilation of the heart after myocardial infarction; to attach another material to a tissue; to augment sutures or staples; to distribute forces across tissue; to prevent leaks; as a barrier membrane on the skin to prevent evaporation of water from burnt skin; as a patch for delivery of anti-scar or antimicrobial medication; to attached devices to tissue; to attach devices to mucus membrane as a tape to secure devices within an oral cavity, such as to hold dentures and oral appliances; as a tape to anchor soft tissue to bone; and, preventing the formation of holes in tissue, enhancing/augmenting mechanical properties of tissues, etc.

B. Delivery of Bioactive Molecules

The composition according to the invention described may also contain one or more pharmaceutical, therapeutic, prophylactic, and/or diagnostic agents that are released during the time period that the material functions as a sealant/adhesive. The agent may be a small molecule agent, for example having molecular weight less than 2000, 1500, 1000, 750, or 500 Da, a biomolecule, for example peptide, protein, enzyme, nucleic acid, polysaccharide, growth factors, cell adhesion sequences such as RGD sequences or integrins, extracellular matrix components, or combinations thereof. Exemplary classes of small molecule agents include, but are not limited to, anti-inflammatories, analgesics, antimicrobial agents, and combinations thereof. Exemplary growth factors include, without limitation, TGF-β, acidic fibroblast growth factor, basic fibroblast growth factor, epidermal growth factor, IGF-I and II, vascular endothelial-derived growth factor, bone morphogenetic proteins, platelet-derived growth factor, heparin-binding growth factor, hematopoetic growth factor, peptide growth factor, or nucleic acids. Exemplary extracellular matrix components include, but are not limited to, collagen, fibronectin, laminin, elastin and combinations thereof. Proteoglycans and glycosaminoglycans can also be covalently or non-covalently associate with the composition of the present invention.

Functional groups on the pre-polymer that were not activated may be used to covalently attach one or more agents, such as small molecule agents and/or biomolecules. Alternatively, the one or more agents can be physically entrapped within the cured composition by curing the composition in the presence of the agent.

C. Tissue Support

The materials can be used to create tissue supports by forming shaped articles within the body to serve a mechanical function. The shaped articles may be produced by a variety of fabrication techniques know in the art, including 3D printing. Such articles may exert functions such as holding two tissues together or positioning the tissue in a specific position inside or outside the body.

The tissue can be coated with a layer of the materials, for example the lumen of a tissue such as a blood vessel to prevent restenosis, reclosure or vasospasm after vascular intervention.

The composition may also contain one or more types of cells, such as connective tissue cells, organ cells, muscle cells, nerve cells, and combinations thereof. Optionally, the material is seeded with one or more of tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, and bone-forming cells. The combination of cells with the material may be used to support tissue repair and regeneration.

D. Anti-Adhesion Barriers

The materials herein described can be applied to reduce or prevent the formation of adhesions after surgical procedures. For example, to prevent adhesion of brain tissue to the skull after brain surgery or implantation of devices or to prevent peritoneal adhesion E. Other Applications The compositions can also be used to coat tools, such as surgical instruments, for example forceps or retractors, to enhance the ability of the tools to manipulate objects. The materials can also be used herein can also be used in industrial applications where it is useful to have a degradable adhesive that is biocompatible, for example to reduce potential toxicity of the degradation products, such as marine applications, for example in underwater use or attaching to the surface of boats. The materials can be also used to produce shaped objects by a variety of techniques known in the art, including 3D printing. The shaped object may have micro or nanoscale resolution.

The present invention will now be illustrated, but in no way limited, by reference to the following examples.

EXAMPLES

All chemicals were acquired from Sigma-Aldrich and used as received unless specified otherwise. The following general protocol was initially applied to synthesize poly glycerol sebacate (PGS) pre-polymer:

1. Equimolar amounts of glycerol and sebacic acid were weighed.
2. The reaction mixture temperature set between 120 and 130° C. until the monomers were completely melted.
3. Upon melting of the reagents the bath or reaction temperature was reduced to the target value of 120° C. and stirring started.
4. The air inside the flask was replaced with nitrogen using three vacuum/purging cycles.
5. The reaction was followed for 8 hours.
6. The nitrogen supply was then removed and the pressure reduced using a vacuum pump set to a target of 15 mBars.

The reaction was followed until the targeted Mw (about 3000 Da) and polydispersity (<3) were achieved. The glycerol:sebacid acid molar ratio targeted was 1:1.

A. Examples for PGSA with Grafted Anhydrides

The following procedure for the manufacture of PGSA containing anhydrides was followed for Examples 1 to 4:

1. PGS pre-polymer was synthesized as described above.
2. Overnight acrylation of PGS pre-polymer with AcCl (0.8 mL per 5 grams of polymer) in 10% w/v DCM in the presence of DMAP (1 mg per gram of polymer), TEA (1.4 mL per 5 grams of polymer) and 200 ppm BHT. The quantities of AcCl and TEA can be adjusted to achieve different degrees of acylation.
3. Overnight acylation with ethanoyl chloride in the presence of DMAP, TEA and 200 ppm BHT. An excess with ethanoyl chloride (1.8 mL per 5 grams of polymer) and TEA (3.5 mL per 5 grams of pre-polymer) is used to achieve hydroxyl blockage. Hydroxyl blockage is evaluated at the end of the synthesis through NMR.
4. Purification by one of the following:
   Three water washing
   Three salted water washing (300 g/L sodium chloride aqueous solution)
   Solvent change to ethyl acetate followed by salt filtration
   Solvent change to ethyl acetate followed by filtration and one salted water washing (300 g/L sodium chloride aqueous solution)
5. Addition of 400 ppm BHT
6. Partial solvent evaporation to reach 50% w/w solution in DCM followed by the addition of 200 ppm of MEHQ and storage at 4° C.
7. Incorporation of Irgacure 2959 and solvent removal through supercritical $CO_2$ Example 1 purification step was water washing. Example 2 purification step was salted water washing. Example 3 purification step was filtration. Example 4 purification step was salted water washing The stability in terms of Mw change of the 50% w/w solutions in DCM is shown in FIG. 1.

Figure 2:
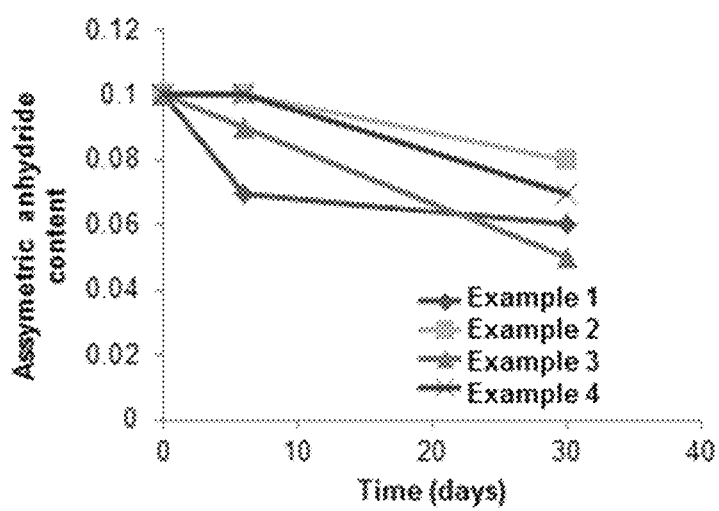
FIG. 2 is a graph displaying the change in asymmetric anhydride content over time for compositions according to the present invention.
Figure 3:
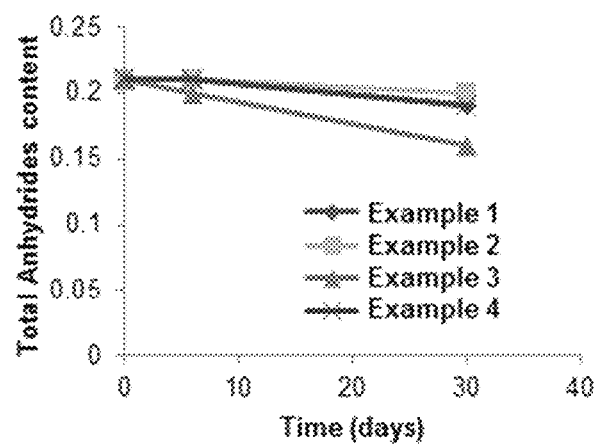
FIG. 3 is a graph displaying the change in total anhydride content over time for compositions according to the present invention.

Anhydride content is shown in FIGS. 2 and 3.

Overall, Example 1 had the highest Mw growth as determined through gel permeation chromatography equipped with a refractive index detector (GPC) and, while filtrated and/or salted water solutions showed improved stability during both synthesis and storage.

Figure 4:
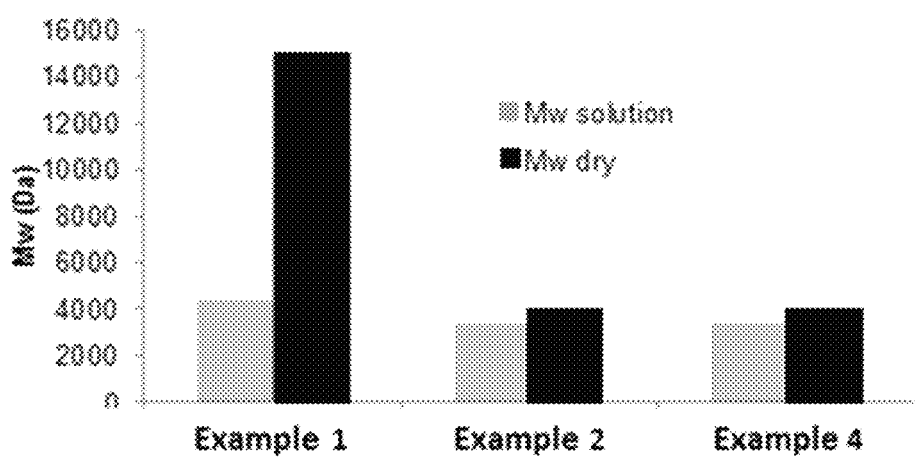
FIG. 4 is a graph displaying Mw in solution and after extraction (dry) for compositions according to the present invention.
Figure 5:
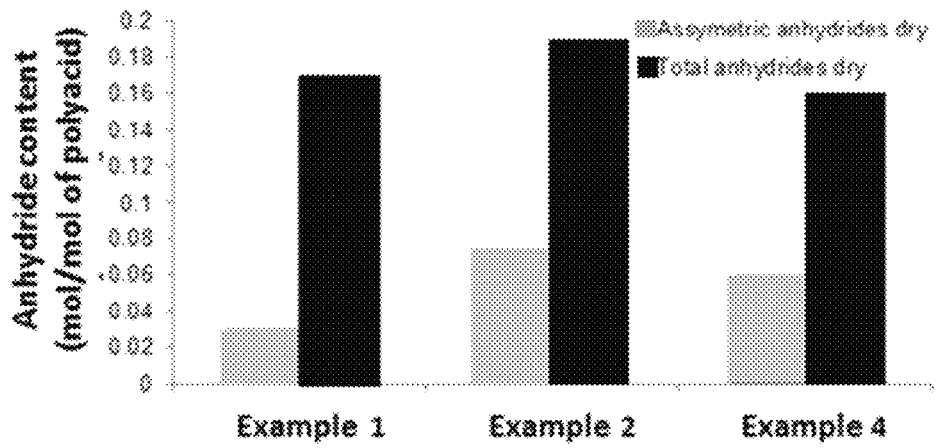
FIG. 5 is a graph displaying the content of asymmetric anhydrides and total content of anhydrides for dry compositions according to the present invention.
Figure 6:
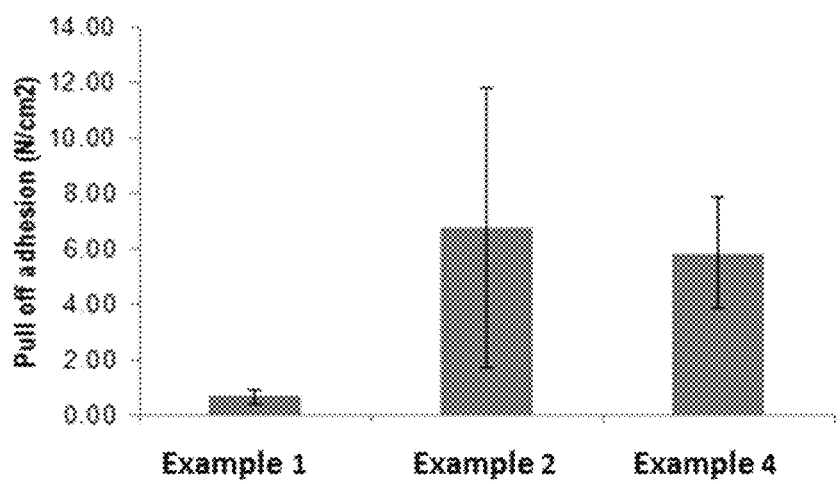
FIG. 6 is a graph displaying adhesion for compositions according to the present invention.

Solutions synthesized for Examples 1, 2 and 4 were extracted from the DCM solution using supercritical $CO_2$ at 40° C. for solvent and impurities removal. Levels of residual solvents below 500 ppm were achieved. Higher Mw increase, measured through GPC, and lower asymmetric anhydride content, measured through NMR upon supercritical extraction of the water washed sample were observed as shown in FIGS. 4 and 5.

The GPC equipment used had the following specifications:
Column—LT6000L, (300×8) mm, 10 m equipped with a precolumn CLM3008 (10×4.6) mm
Flow rate—1.0 mL/min
Injection volume—100 μL
Column temperature—35° C.
Refractometer temperature—35° C.
Elution mode—Isocratic
Mobile phase—Tetrahydrofuran (THF)
Adhesion Testing Examples were tested for pull-off adhesion according to the following pull off method. Pull-off adhesion testing (at 900) was performed on an Instron with fresh porcine epicardial tissue. The tissue was kept in phosphate-buffered saline to assure that it remained wet during testing. Unless specified, a poly glycerol sebacate urethane (PGSU) patch was used for testing and was about 200 mm thick and 6 mm in diameter. A thin layer of the example composition, with a thickness of about 200 μm, was applied to the patch material before adhesion testing. During the curing process, a compressive force of −3 N was applied to the example composition coated patch with a non-adhesive material (borosilicate glass rod 9 mm in height) connected to the UV light guide (Lumen Dynamics Group Inc) with standard adhesive tape around both the glass rod and the light guide. The interposition of the borosilicate glass rod facilitates the release of the curing system from the patch without disturbing the patch/adhesive-tissue interface. The pull-off procedure involved grip separation at a rate of 8 mm/min, causing uniform patch detachment from the tissue surface. Adhesion force was recorded as the maximum force observed before adhesive failure, when a sharp decrease in the measured stress was observed.

Figure 7:
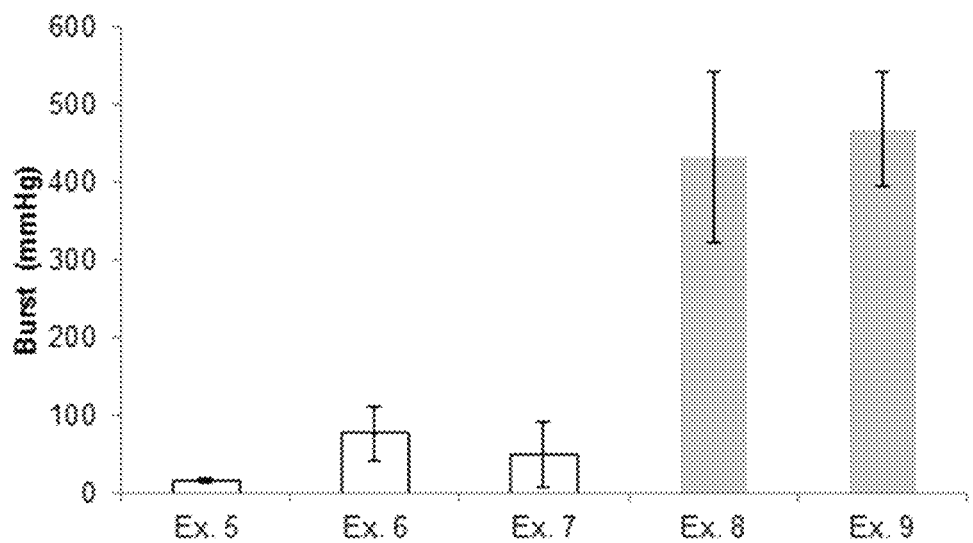
FIG. 7 is a graph displaying burst performance for compositions according to the present invention and for comparative examples.

Pull off adhesive performance of the dry product after supercritical $CO_2$ treatment is shown in FIG. 7. Overall, pull off performance is enhanced for higher content of asymmetric anhydrides.

Burst Performance Testing

Figure 8:
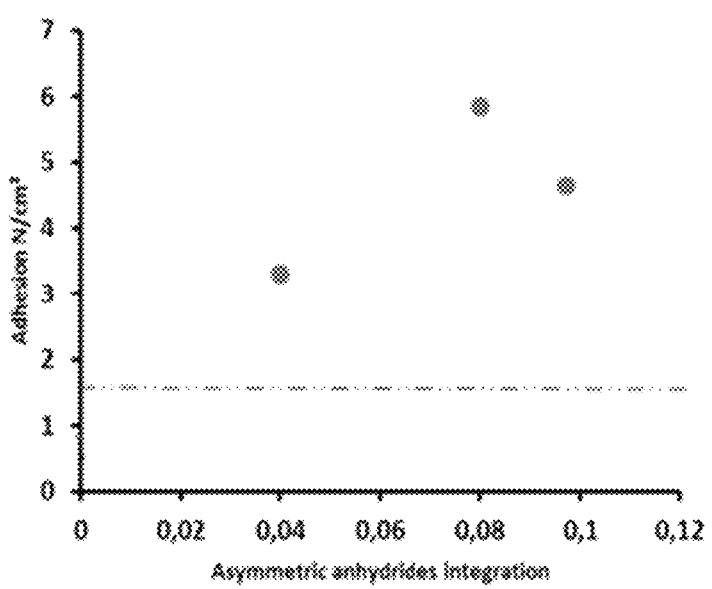
FIG. 8 is a graph displaying the correlation between adhesive properties and anhydride content for compositions according to the present invention.

Burst performance of the dry product after the supercritical $CO_2$ stage is shown in FIG. 8. PGSA burst performance was evaluated to seal a 5 mm in diameter ePTFE graft sutured to porcine carotid artery. Before glue application, the suture line started leaking at about 10 mmHg. Approximately 0.2 mL of PGSA was applied around the suture line using a syringe and the formulation was cured with light for approximately 1 minute. The burst performance is enhanced and the pressure at which the suture line started leaking was measured. Comparative example 5 was Fibrin. Comparative examples 6 and 7 were PGSA polymers without anhydrides (produced through ethanol capping) with degrees of acrylation of approximately 0.3 and 0.5 mol/mol of glycerol, respectively.

An increased adhesion force is obtained for polymer with increased anhydride content and blocked hydroxyl groups. This can be seen in FIG. 8 for examples according to the present invention (synthesized in accordance with example 2), where the line represents the average adhesion force previously reported for preferred compositions of hydrophobic light activated adhesive compounds by Lang et al.

The results obtained are summarized in the table below (+ represents good, ++ represents very good, +++ represents excellent, − represents poor):

|  | Adhesion | Stability |
| --- | --- | --- |
| Anhydrides and free hydroxyls | ++ | − |
| No Anhydrides and free hydroxyls | − | ++ |
| Anhydrides and no free hydroxyls | +++ | + |

The results demonstrate that increase anhydride content increases pull-off adhesion, particularly when there are no free hydroxyl groups.

Figure 9:
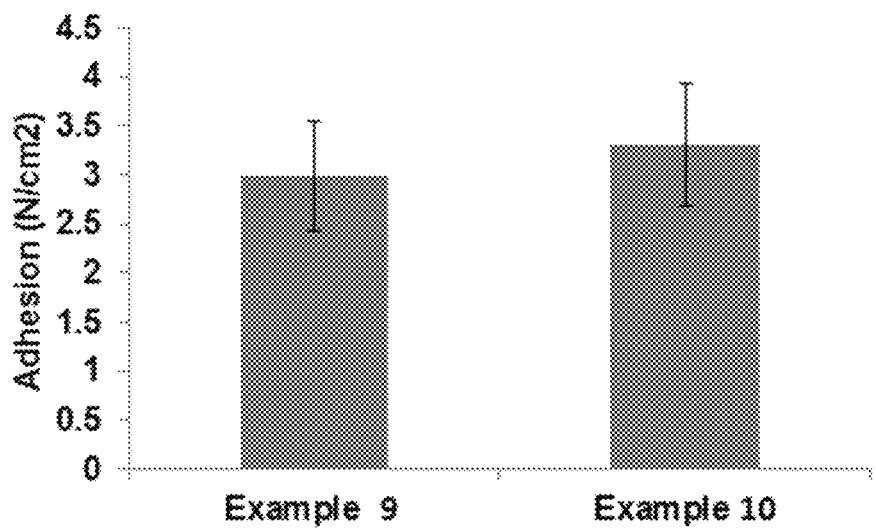
FIG. 9 is a graph displaying the adhesion of different batches produced using a method according to the present invention.
Figure 10:
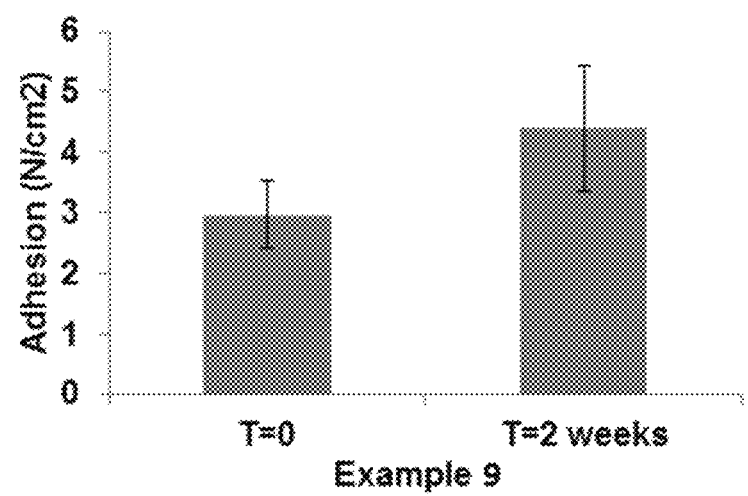
FIG. 10 is a graph displaying the adhesion over time for produced using a method according to the present invention.

The manufacturing reproducibility was evaluated. All procedures were described as reported above, except that DMAP was not utilized as catalyst as this is known to interfere with anhydride stability. The manufacturing reproducibility was higher when the purification consisted of filtration followed by a salted water wash, to assure maintenance of anhydrides content and removal of any impurities, such as trimethylamine hydrochloride formed as the reaction by-product. FIG. 9 shows the pull off adhesion performance for two batches (example 9 and 10) produced according to this protocol. The adhesion of the product was also maintained during storage, as shown in FIG. 10. It is demonstrated that a preferred method for product purification is filtration with salted water wash and that the reaction can be conducted without the use of DMAP.

It has also been determined that strongly adhesive batches can be produced even if:

1. The addition of TEA is performed first, followed by the dropwise addition of acryloyl chloride over two hours followed by reaction for 1 hour, followed by the dropwise addition of ethanoyl chloride over two hours followed by reaction for 1 hour. The purification method used for the production of these materials was filtration only, and no DMAP was used during the reaction. Irgacure TPO (diphenyl(2,4,6-trimethylbenzoyl)-phosphine oxide) is used as photoinitiator, instead of Irgacure 2959.
2. The addition of TEA is performed in parallel to acryloyl chloride over two hours followed by reaction for 1 hour, followed by the dropwise parallel addition of TEA ad ethanoyl chloride over two hours followed by reaction for 1 hour. The purification method used for the production of these materials was filtration only, and no DMAP was used during the reaction. Irgacure TPO (diphenyl(2,4,6-trimethylbenzoyl)-phosphine oxide) is used as photoinitiator, instead of Irgacure 2959.
3. The addition of acryloyl chloride, trimethylamine and ethanoyl chloride is performed in parallel dropwise over 2 hours, followed by reaction for 1 hour. The purification method used for the production of these materials was filtration only, and no DMAP was used during the reaction. Irgacure TPO (diphenyl(2,4,6-trimethylbenzoyl)-phosphine oxide) is used as photoinitiator, instead of Irgacure 2959.

B. Examples for PGSA Mixed with Non-Grafted Anhydrides

On a different approach, the adhesive strength of PGSA without grafted anhydrides is enhanced by mixing with anhydride monomers.

PGSA without anhydrides is synthesized with an additional step of ethanol capping after pre-polymer activation to remove grafted anhydrides from the polymer backbone as described above.

Purification is conducted through water washing.

Example 11

PGSA without anhydrides with a degree of acrylation of ~0.5 mol/mol of glycerol with 4% w/w of methacrylic anhydride, incorporated through mixing with the dry product.

Example 12

PGSA without anhydrides with a degree of acrylation of ~0.25 mol/mol of glycerol with 4% of methacrylic anhydride.

Example 13

PGSA without anhydrides with a degree of acrylation of ~0.5 mol/mol of glycerol with 2% of mono acrylate (Ethyl acrylate), incorporated through mixing with the dry product.

Example 14

PGSA without anhydrides with a degree of acrylation of ~0.5 mol/mol of glycerol with 2% of diacrylate (1,4-butandiol diacrylate), incorporated through mixing with the dry product.

Example 15

PGSA without anhydrides with a degree of acrylation of ~0.5 mol/mol of glycerol with 5% of acrylic anhydride, incorporated through mixing with the dry product.

Example 16

PGSA without anhydrides with a degree of acrylation of ~0.5 mol/mol of glycerol with 5% of acetic anhydride, incorporated through mixing with the dry product.

Figure 11:
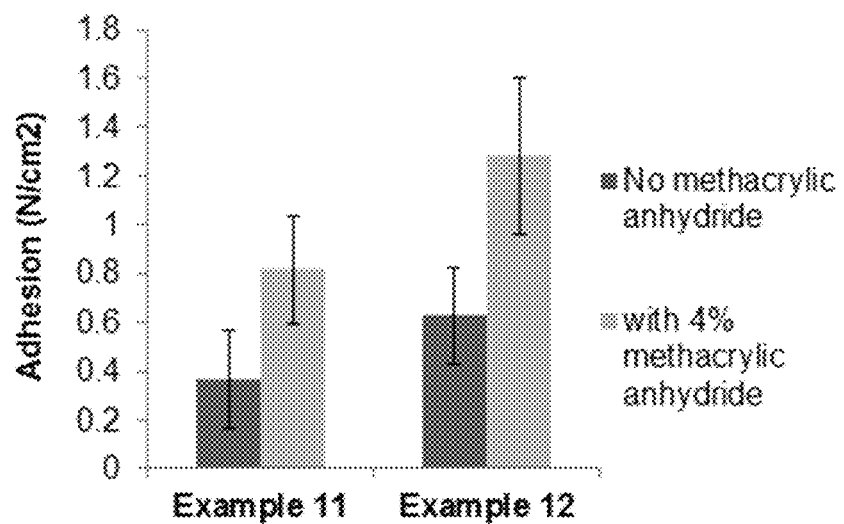
FIG. 11 is a graph displaying the adhesive properties for composition according to the present invention including non-grafted anhydrides, in comparison with doping of methacrylic anhydride monomer.

As shown in FIG. 11, methacrylic anhydride is able to enhance the adhesive properties of PGSA without grafted anhydrides.

Figure 12:
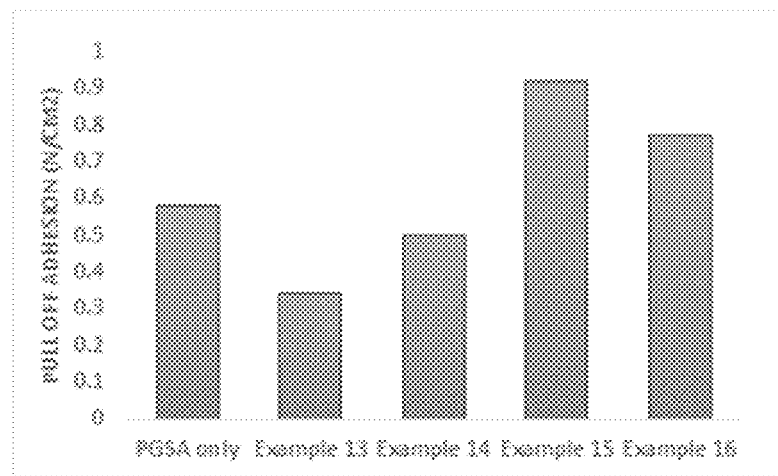
FIG. 12 is a graph displaying the adhesive properties for composition according to the present invention including non-grafted anhydrides, in comparison with doping of acrylate or anhydride monomers.

As shown in FIG. 12, addition of acrylic anhydride is able to enhance the adhesive properties of PGSA without grafted anhydrides (see Examples 15 and 16). In contrast, addition of mono or diacrylate monomers (without anhydride function) have minimal impact on the adhesive performance of PGSA (see Examples 13 and 14, respectively).

The invention claimed is:

1. An adhesive composition comprising:
an activated pre-polymer comprising a polymeric unit of the general formula $(-A-B-)_n$, wherein A represents a moiety derived from a polyol, B represents a moiety derived from a polyacid, and n represents an integer equal to or greater than 1,
wherein said pre-polymer comprises one or more grafted anhydride moieties, and
wherein the molar ratio of said one or more grafted anhydride moieties to B is about 0.1 mol/mol or greater.

2. The composition according to claim 1, further comprising a second pre-polymer having the general formula (I):

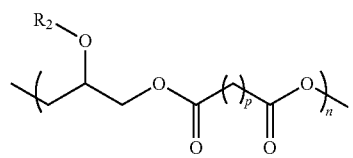

wherein n and p each independently represents an integer equal or greater than 1, and wherein $R_2$ in each individual unit represents hydrogen or a polymer chain or —C(=O)—$CR_3$=$CR_4R_5$, wherein $R_3$, $R_4$, and $R_5$ each independently represents H, alkyl, aryl, substituted alkyl, substituted aryl, carboxylic acid, ester, amide, amine, urethane, ether, or carbonyl.

3. The composition according to claim 2, wherein p is an integer from 4 to 10.

4. The composition according to claim 3, wherein p is 8.

5. The composition according to claim 4, wherein the second pre-polymer of general formula (I) has the following formula:

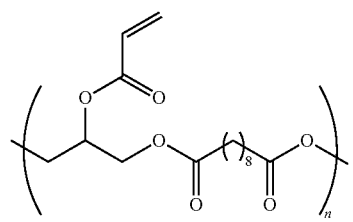

wherein n represents an integer equal or greater than 1.

6. The composition according to claim 1, wherein said pre-polymer has the general formula (II):

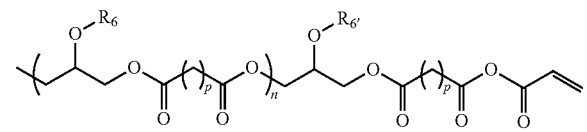

wherein p and n each independently represents an integer equal or greater than 1, and
wherein $R_6$ and $R_{6'}$ each independently represents:
  (i) a polymer chain; or
  —C(=O)—$CR_3$=$CR_4R_5$, where $R_3$, $R_4$, and $R_5$ each independently represents H, alkyl, aryl, substituted alkyl, substituted aryl, carboxylic acid, ester, amide, amine, urethane, ether, or carbonyl; or
  (iii) alkyl, aryl, heterocycles, cycloalkyl, aromatic heterocycles, multicycloalkyl, ester, ether, halide, carboxylic acid, amino, alkylamino, dialkylamino, trialkylamino, amido, carbamoyl, thioether, thiol, alkoxy, or ureido groups.

7. The composition according to claim 6, wherein said pre-polymer has the following formula:

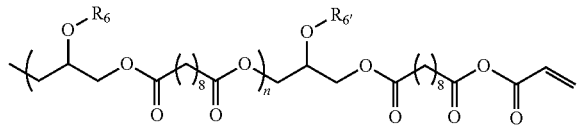

wherein $R_6$ and $R_{6'}$ each independently represents a polymer chain,

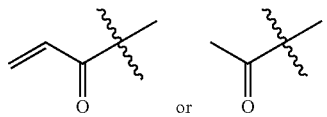

8. The composition according to claim 1, wherein the molar ratio of said one or more grafted anhydride moieties to B is greater than 0.1 mol/mol.

9. The composition according to claim 1, wherein the pre-polymer comprises an asymmetric anhydride, wherein a molar content of the asymmetric anhydride is greater than about 30% of a total content of said one or more grafted anhydrides moieties.

10. The composition according to claim 1, wherein the pre-polymer comprises no free hydroxyl group.

11. The composition according to claim 1, further comprising a photo-initiator.

12. The composition according to claim 11, wherein the composition when cured with light in the presence of a photo-initiator has a 90° pull off strength greater than about 1.5 N/cm².

13. The composition according to claim 12, wherein the composition has a 90° pull off strength of about 2 to about 7 N/cm².

14. The composition according to claim 11, wherein the composition when cured with light in the presence of a photo-initiator has a burst performance of greater than about 200 mmHg.

15. The composition according to claim 14, wherein the composition has a burst performance of about 400 to about 500 mmHg.

16. The composition according to claim 1, wherein the polymeric unit is activated with a vinyl-containing group.

17. The composition according to claim 1, wherein the pre-polymer contains nucleophilic groups that are protected.

18. The composition according to claim 6, wherein $R_6$ and $R_{6'}$ each independently represents: —C(=O)—CH=CH$_2$ or —C(=O)—CH$_3$.

19. A method for manufacturing a composition according to claim 1, said method comprising:
i) polycondensing a first component comprising a substituted or unsubstituted polyol and a second component comprising a substituted or unsubstituted polyacid to form a pre-polymer comprising one or more hydroxyl groups;
ii) reacting the pre-polymer with an activating agent to form an activated pre-polymer comprising one or more grafted anhydride moieties; and
iii) protecting the one or more remaining free hydroxyl groups on the activated pre-polymer with a blocking group, wherein the blocking group is not —C(=O)—CH=CH$_2$.

20. The method according to claim 19, wherein the method further comprises a step of purifying the activated pre-polymer.

21. The method according to claim 20, wherein the method further comprises the step of adding an anhydride compound after the step of purifying the activated pre-polymer.

22. The method according to claim 19, wherein the first component comprises glycerol.

23. The method according to claim 19, wherein the second component comprises sebacic acid.

24. The method according to claim 20, wherein the step of purifying comprises filtering and/or washing with salt water.

25. The method according to claim 19, wherein the free hydroxyl groups on the activated pre-polymer are blocked through an acylation reaction.

26. The method of claim 19, wherein the blocking group is selected from acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; or cyclic or acylic, branched or unbranched, substituted or unsubstituted heteroalkynyl; substituted or unsubstituted aryl; and substituted or unsubstituted heteroaryl.

27. The method of claim 19, wherein the blocking group is —C(=O)—CH$_3$.

28. The method of claim 19, wherein the activating agent comprises —C(=O)—CR$_1$ =CR$_2$R$_3$, wherein R$_1$, R$_2$, R$_3$ are independently from one another, selected from H, alkyl, aryl, substituted alkyl, substituted aryl, carboxylic acid, ester, amide, amine, urethane, ether, and carbonyl.

29. The method of claim 28, where the activating agent is acryloyl chloride.

30. A method of curing the composition according claim 1, comprising curing the composition with light in the presence of a photo-initiator.

31. A cured composition obtained by the method according to claim 30.

32. A method for adhering or sealing tissue, comprising applying the composition of claim 1 to the surface of the tissue and curing the composition.

33. A method for adhering tissue to the surface of a medical device, comprising applying the composition of claim 1 to the surface of the tissue and/or medical device and curing the composition.

34. An adhesive composition comprising:
an activated pre-polymer comprising a polymeric unit of the general formula (-A-B-)$_n$, wherein A represents a moiety derived from a polyol, B represents a moiety derived from a polyacid, and n represents an integer equal to or greater than 1,
wherein said pre-polymer comprises one or more grafted anhydride moieties,
wherein said composition comprises two or more hydroxyl groups, at least one hydroxyl group being activated with —C(=O)—CR$_3$=CR$_4$R$_5$ and at least one hydroxyl group being protected by a blocking group that is not —C(=O)—CR$_3$=CR$_4$R$_5$, where R$_3$, R$_4$, and R$_5$ each independently represents H, alkyl, aryl, substituted alkyl, substituted aryl, carboxylic acid, ester, amide, amine, urethane, ether, or carbonyl, and wherein the molar ratio of said one or more grafted anhydride moieties to B is greater than about 0.1 mol/mol.

35. The composition according to claim 34, wherein the pre-polymer comprises no free hydroxyl group.

36. The composition according to claim 34, wherein the blocking group is selected from acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; and substituted or unsubstituted heteroaryl.

37. The composition according to claim 34, wherein the blocking group is —C(=O)—CH$_3$.

38. The composition according to claim 34, wherein the composition has a 90° pull off strength of about 2 to about 7 N/cm$^2$.

39. The composition according to claim 34, wherein the composition when cured with light in the presence of a photo-initiator has a burst performance of greater than about 200 mmHg.

40. The composition according to claim 34, wherein the composition has a burst performance of about 400 to about 500 mmHg.

41. The composition according to claim 34, wherein the molar ratio of said one or more grafted anhydride moieties to B is greater than about 0.05 mol/mol.

42. The composition according to claim 34, wherein A is glycerol and B is sebacic acid.

* * * * *